United States Patent [19]

Ino et al.

[11] Patent Number: 4,724,320
[45] Date of Patent: Feb. 9, 1988

[54] METHOD OF OBSERVING THE ARRANGEMENT OF ATOMS ON A SURFACE AND APPARATUS THEREFOR

[75] Inventors: Shozo Ino, Tokyo; Hiroshi Daimon, Chiba; Shuji Hasegawa, Kokubunji, all of Japan

[73] Assignee: Shozo Ino, Tokyo, Japan

[21] Appl. No.: 779,902

[22] Filed: Sep. 25, 1985

[30] Foreign Application Priority Data

Sep. 26, 1984 [JP] Japan .............................. 59-200955

[51] Int. Cl.$^4$ .............................................. H01J 37/26
[52] U.S. Cl. ..................................... 250/307; 250/310
[58] Field of Search ............... 250/306, 307, 310, 309, 250/311, 442.1

[56] References Cited

U.S. PATENT DOCUMENTS

| | | | |
|---|---|---|---|
| 3,209,146 | 9/1965 | Shirai | 250/442.1 |
| 3,333,100 | 7/1967 | Cilyo | 250/310 |
| 3,848,126 | 11/1974 | Swindells et al. | 250/272 |
| 3,942,005 | 3/1976 | Wanatabe | 250/310 |
| 3,963,922 | 6/1976 | Zulliger et al. | 250/272 |
| 4,037,101 | 7/1977 | Okumura et al. | 250/310 |
| 4,514,629 | 4/1985 | Smith et al. | 250/311 |

FOREIGN PATENT DOCUMENTS

52-58355  5/1977  Japan .

OTHER PUBLICATIONS

The London Edinburgh and Dublin Philosophical Magazine and Journal of Science, vol. XLV (6th Series), p. 1121 (1923).
The Crystalline-State, Vol. II, The Optical Principles of the Diffraction of X-Rays, R. 166–175, G. Bell and Sons, Ltd., (1965).
Handbook of Synchrotron Radiation, 1A, p. 265, Amsterdam (1983).
X-ray Microanalyzer, Vchiyamz et al., Nikkan Kogyo Shinbun Ltd., Tokyo, 8th Edition, Jan. 1978.
Japanese Journal of Applied Physics, vol. 19, No. 8, Aug., 1980, pp. 1451–1457.

Primary Examiner—Carolyn E. Fields
Assistant Examiner—Paul A. Guss
Attorney, Agent, or Firm—Armstrong, Nikaido, Marmelstein & Kubovcik

[57] ABSTRACT

A method for observing the arrangement of atoms in a thin layer on a surface and an apparatus for employing the method are disclosed. According to the method, a finely converged electron beam is directed to a surface of a sample and the X-ray emitted from the surface is detected at a take-off angle equivalent to, or in the vicinity of, the total reflection angle, thereby avoiding interference from X-rays emitted beneath the surface. The apparatus includes an electron gun, a sample holding means, one or more detectors and devices for storing, processing and displaying the output signal from the detectors. The apparatus also provides for two-dimensional scanning of a surface and for adjustment of the position of the sample and of the detectors.

3 Claims, 5 Drawing Figures

METHOD OF OBSERVING THE ARRANGEMENT OF ATOMS ON A SURFACE AND APPARATUS THEREFOR

BACKGROUND OF THE INVENTION

This invention relates to a method of and apparatus for observing the arrangement of atoms on a surface, in which an electromagnetic wave produced from the surface of a sample by irradiating an electron beam on the surface of the sample is detected utilizing the total reflection of the electromagnetic wave on the surface of the sample, the scanned image being displayed.

It is known that a superlattice structure which is peculiar to the surface of a crystal and completely different from that in the interior of a crystal is formed on the clean surface of the crystal of a semiconductor or a metal, or on such a surface with one atomic layer of metal or the like absorbed. However, the concrete arrangement or positions of atoms, namely the surface structure of atoms, has been little clarified. For example, an ultrastructure called "7×7 structure" which has seven times as many unit cells as the bulk structure is formed on the surface of Si(111). Great interest has been aroused in the arrangement of the atoms in the 7×7 structure, and study on it has been carried out by various means. Among these, a typical means for observing the arrangement of atoms will be described in the following.

An electron microscope, a scanning electron microscope, a field ion emission microscope, and the like are known as apparatuses with high resolution for obtaining a magnified image of a substance.

The electron microscope or the scanning microscope produces an image of the potential of an atom projected in the direction in which the electron beam scans. Therefore, if the electron beam enters in the direction of a specific axis of a crystal, many atoms overlap in this direction, thereby constituting an atom column, and the lattice image of the crystal with their potentials overlapped can be observed. In other words, this image is the image of the atoms arranged in the form of a column, not an image of the respective atom. In addition, even this lattice image cannot be obtained except when the electron beam enters in parallel to the crystallographic axis. That is, it is difficult to observe the image of the respective atom with an electron microscope or a scanning electron microscope.

On the other hand, though the image of the arrangement of the respective atom can be observed with a field ion emission microscope (F I M), the object of the observation is limited to high-melting-point metals such as W, Mo, and Ta, and it is difficult to observe the image of the arrangement of atoms in other substances. In addition the image of an individual atom cannot be obtained with an electron microscope, a scanning microscope or a field ion emission microscope.

There is a method of detecting the X-rays radiated from the vicinity of the surface of a sample by irradiating an electron beam on the surface of the sample with an electron probe X-ray micro analyzer (X M A). However, since the angle between the X-ray and the sample is ordinarily large, at least 30°, and hence the stereoscopic angle to be detected is also large, about 10°, not only the X-rays from the element on the surface of the sample but also the X-rays from the elements in the bulk are detected simultaneously. The thickness of the bulk portion to be detected at the same time with the surface reaches as deeply as several μm (several tens of thousands of Å) from the surface, so that the X-rays in the several atomic layers from the surface are buried in the X-rays from the bulk. This method enables an image of an individual element to be obtained, but the resolution at present is about 5,000 Å. Furthermore, even if an electron beam is finely converged, it scatters in the sample and detects the X-ray at a position about several μm from the surface, and high resolution is not obtained.

Auger electron spectroscopy (A E S) is a method of elemental analysis on a surface by irradiating an electron beam on the surface of a sample and utilizing the Auger effect of the electron beam. This method is said to be the most efficient in sensitivity, but, inconveniently, this is applicable only to elements of a smaller atomic number and the sensitivity remarkably decreases with respect to elements of a large atomic number.

Recently a method of using reflection high energy electron diffraction (RHEED) was reported. (Shozo Ino et al.: Japanese Journal of Applied Physics Vol. 19, No 8, 1980, pp1451–1457). This is a method of irradiating a high energy electron beam on the surface of a sample and detecting the specific X-ray produced from the element on the surface of the sample. The X-ray take-off angle is 3° to 5°, and the intensity of the specific X-ray is inferior in comparison with that in Auger electron spectroscopy.

The inventors of the present invention proposed a method of analyzing an element on a surface by utilizing a method of detecting an electromagnetic wave at the total reflection angle thereof. This is a method of detecting the electromagnetic wave radiated from the vicinity of a surface by excitation of an electron beam by utilizing the total reflection of the electromagnetic wave. By this method the electromagnetic wave radiated from an atom on the outermost surface can be detected with great sensitivity. Accordingly, in analyzing an element, analysis results of high sensitivity are obtained in relation to the outermost surface.

An Auger electron microscope obtains a scanned image on the basis of the above-described principle on elemental analysis, but at present the resolution is not so good. That is, since low energy Auger electrons which are emitted from the depth of a sample cannot reach the surface, those emitted from the vicinity of the surface are chiefly detected. However, the size of an Auger electron signal is ordinarily smaller than that of the background consisting of the secondary electrons, and S/N (the ratio of signal and noise) is low, so that the resolution of the Auger electron microscope which uses these Auger electrons as signals is not so good, and is now about 5,000 Å.

As described above, when observing the arrangement of atoms on the clean surface of a semiconductor or a metal, or such surface with an atomic first layer of metal absorbed thereon, the conventional methods cannot bring about satisfactory resolution for the following various reasons: these elements are ordinarily trace elements; since a measuring system gathers information about the elements which constitute the bulk, it is difficult to obtain the information about only the elements in the vicinity of the surface separated from the other elements with an electron microscope or a scanning electron microscope; and the S/N of the Auger electron microscope is low. In addition, the field ion emission microscope is defective in that it can observe the surface of only specific metals.

SUMMARY OF THE INVENTION

Accordingly, it is an object of the invention to provide a method of and apparatus for observing the arrangement of atoms on a surface, based on a new principle utilizing the total reflection of an electromagnetic wave and which enables the arrangement of atoms on several atomic layers from the surface (outermost surface) to be observed.

To achieve this aim, this invention provides a method of observing the arrangement of atoms on a surface comprising the steps of: scanning two-dimensionally the surface of a sample by irradiating a finely converged electron beam thereon; detecting the electromagnetic wave produced from the surface of the sample by the irradiation of the electron beam at a take-off angle equivalent to the total reflection angle of the electromagnetic wave on the surface of the sample or an angle in the vicinity thereof; and forming a scanned image by the detected electromagnetic wave. This invention also provides an apparatus for observing the arrangement of atoms on a surface which detects an electromagnetic wave produced from the surface of a sample by irradiating an electron beam on the surface of the sample and by utilizing the total reflection of the electromagnetic wave on the surface of the sample comprising: sample holding means for holding a sample; electron beam irradiating means which irradiates a fine electron beam on the surface of the sample for two-dimensional scanning; electromagnetic wave detecting means for detecting an electromagnetic wave produced from the elements on the surface of the sample at a take-off angle equivalent to the total reflection angle of the electromagnetic wave on the surface of the sample or an angle in the vicinity thereof; storing means for storing the output signal of the electromagnetic wave detecting means; and signal processing/displaying means for processing the output signal which is stored in the storing means and displaying the scanned image of the surface of the sample.

The method and apparatus for observing the arrangement of atoms on a surface according to the invention which has the above-described structure obtains a scanned image similar to that by an electron probe X-ray microanalyzer (X M A), but it is different from the conventional one in that the detection sensitivity of the electromagnetic wave of atoms on a surface is greatly increased by utilizing a method of detecting an electromagnetic wave at the total reflection angle thereof. The method of analyzing elements on a surface by utilizing this method of detecting an electromagnetic wave at the total reflection angle thereof has been proposed by the inventors of the present invention, on the basis of the phenomenon the inventors found, that if the electromagnetic wave emitted from the vicinity of a surface by the excitation of an electron beam is detected by utilizing the total reflection of the electromagnetic wave, the electromagnetic wave emitted from the atoms on the outermost surface can be detected with greatly improved sensitivity.

The present invention also utilizes the method of detecting an electromagnetic wave at the total reflection angle. An electron beam which is finely converged is caused to scan in the direction x and y, which is parallel to the surface, for the purpose of detecting the electromagnetic wave at a take-off angle equivalent to the total reflection angle of the electromagnetic wave on the surface of a sample or an angle in the vicinity thereof, and of forming the scanned image by the electromagnetic wave, whereby the image of the arrangement of the atoms on the surface is visualized. This method provides a scanned image with about 1,000 times better resolution than the conventional X M A.

DESCRIPTION OF THE PREFERRED EMBODIMENT

Hereinunder an embodiment will be described with reference to the accompanying drawings. Though this invention is used for detecting electromagnetic waves, an X-ray will be cited as an example in the following explanation.

Figure 1:
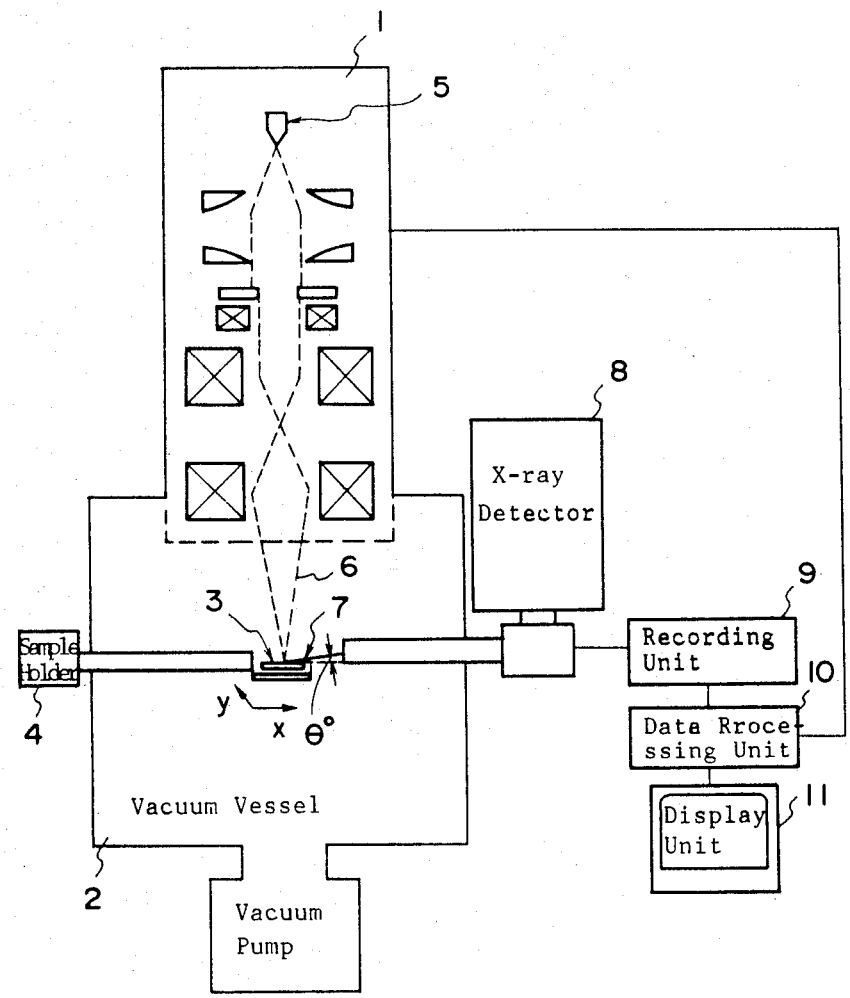
FIG. 1 is a schematic view of the structure of an embodiment of an apparatus for observing the arrangement of atoms on a surface according to the present invention.

FIG. 1 is a schematic view of the structure of an embodiment of an apparatus for observing the arrangement of atoms on a surface according to the invention. In FIG. 1, the reference number 1 denotes an electron beam source, 2 a vacuum vessel, 3 a sample, 4 a sample holder, 5 an electron gun, 6 an electron beam, 7 a radiation X-ray, 8 an X-ray detector, 9 a recording unit, 10 a data processing unit, and 11 a display unit.

The main body of an apparatus for observing the arrangement of atoms on a surface according to the invention is the vacuum vessel 2, which includes the electron beam source 1, and is capable of evacuation to a high vacuum of at least $10^{-5}$ Torr. The apparatus is, as shown in FIG. 1, further composed of the sample holder 4 for holding the sample 3, the electron gun 5 for emitting the electron beam 6, the X-ray detector 8 for detecting and measuring the X-ray 7 with high sensitivity, the recording unit 9 for recording a detection signal of the X-ray detected by the X-ray detector 8, the data processing unit 10 for processing the signal recorded in the recording unit 9, and the display unit for displaying the detection signal of the X-ray processed by the data processing unit 10 as a scanned image of the surface of the sample. It goes without saying that the elctron beam source 1 is provided with a convergent lens, an objective lens, a deflection coil, a stop, and their controlling means, like a general scanning microscope and other scanning analyzing devices, and that it has a faculty of converging the electron beam emitted from the electron gun 5 into a fine and strong beam to make it scan two-dimensionally in the directions x and y, in parallel to the surface of the sample. This invention does not restrict the structure of the electron beam source 1. I is preferable, however, that the electron beam is converged into as fine a beam as possible to form a strongly paralleled and powerful beam. It is also preferable that the sample holder 4 is provided with a drive mechanism which can vary the position and inclination of a sample with a rotary means or translation means which is in general use, such as bellows, and that the X-ray detector 8 is also provided with a drive mechanism which can vary the detection angle (take-off angle) and is composed so as to be controllable so that the the X-ray 7 radiated from the surface of the sample 3 can be detected at the total reflection angle $\theta_0$. (generally small angle) by moving or rotating the sample or shifting the X-ray detecting position. It is also desirable that the X-ray detector 8 can further analyze the energy of the X-ray simultaneously with the detection of the X-ray 7.

In the apparatus for observing the arrangement of atoms on a surface shown in FIG. 1, the electron beam emitted from the electron gun 5 is controlled by the electron beam source 1 and is irradiated onto the surface of the sample 3. When the electron beam is caused to scan two-dimensionally in the direction x and y, in parallel to the surface of the sample 3, the X-ray 7 is radiated from the surface of the sample. The X-ray 7 is detected by the X-ray detector 7 at a take-off angle equivalent to the total reflection angle of the X-ray with respect to the surface of the sample 3 or an angle in the vicinity thereof, whereby only the X-rays radiated from the atoms of the outermost surface are detected with high sensitivity. This is recorded by the recording unit 9, and is processed by the data processing unit (computer) 10, which synchronizes the data with a scanning synchronizing signal of the electron beam and displays the scanned image on the display unit 11.

Figure 2:
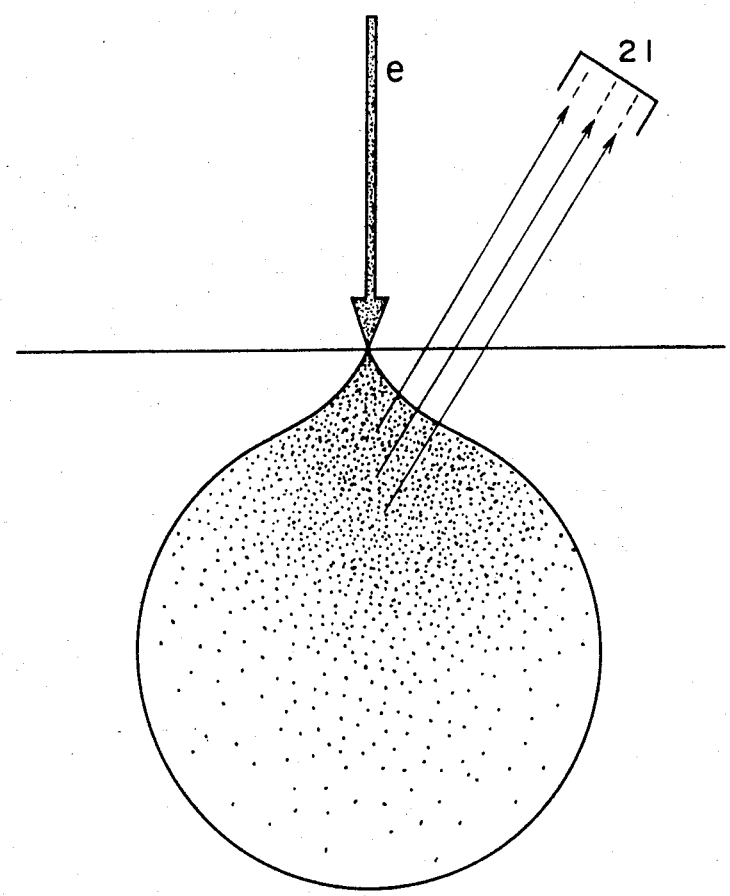
FIG. 2 is an explanatory view of electrons which enter the surface of a sample and are being scattered by the atoms in the specimens.

FIG. 2 illustrates the state in which the electron beam enters the surface of the sample and diffuses while causing multiple scattering.

Figure 3:
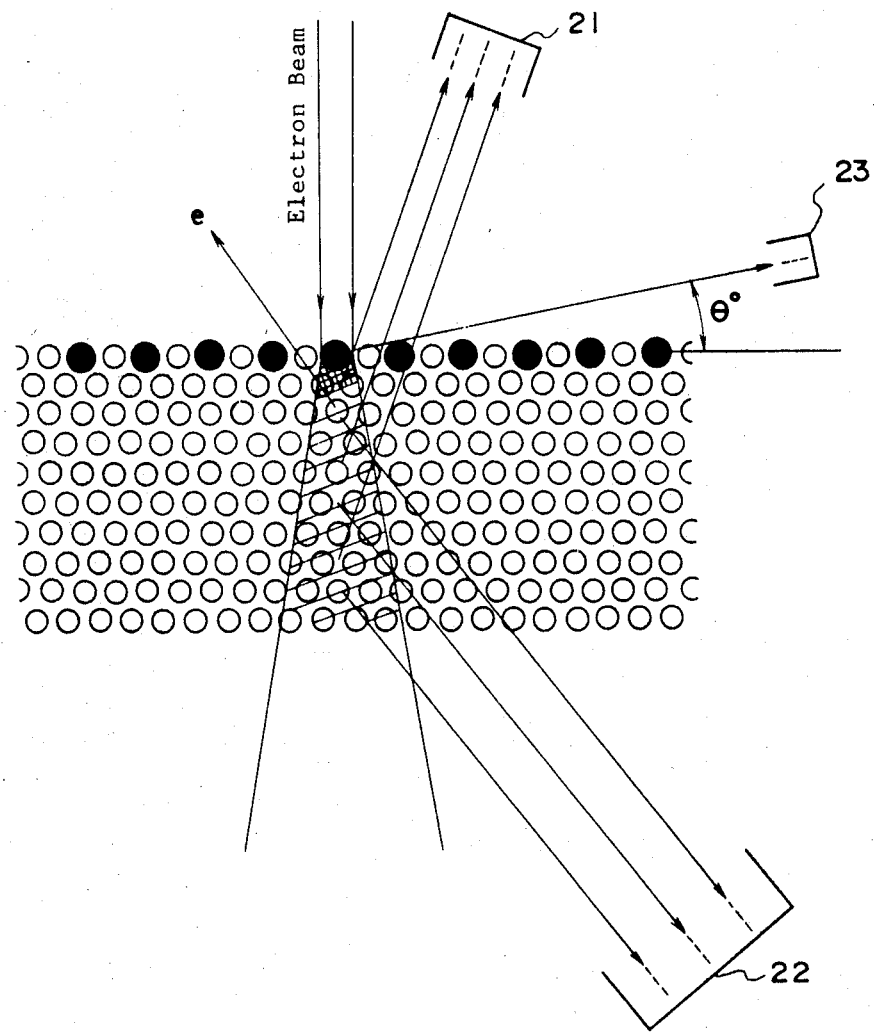
FIG. 3 is an enlarged view of the electrons in the vicinity of the surface shown in FIG. 2, and illustrates the X-rays which are radiated by the excitation of an electron beam and an example of a position for detecting them.
Figure 4:
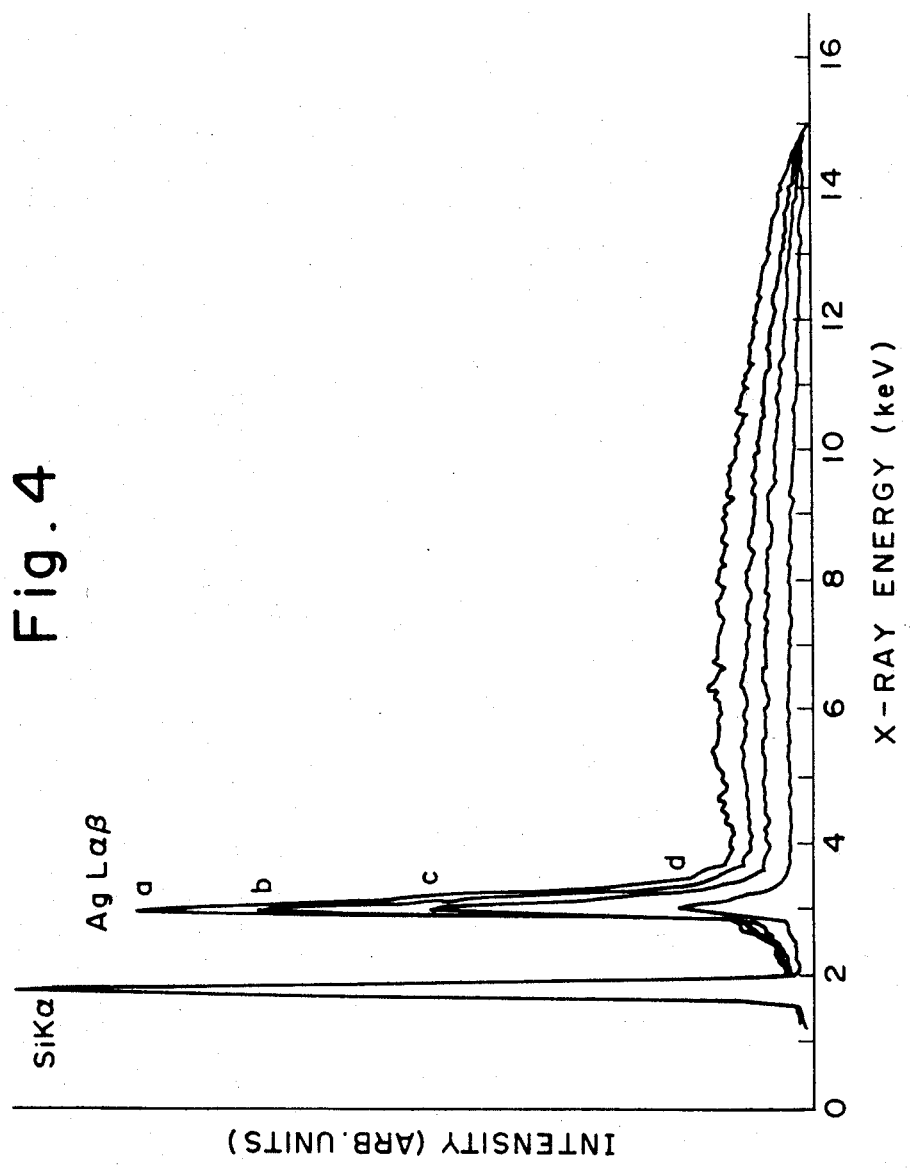
FIG. 4 shows an example of measurement of the distribution of the X-ray energy which is radiated from a sample of Si (111) with Ag 1.2 Å thick (one atomic layer) absorbed on the surface thereof.
Figure 5:
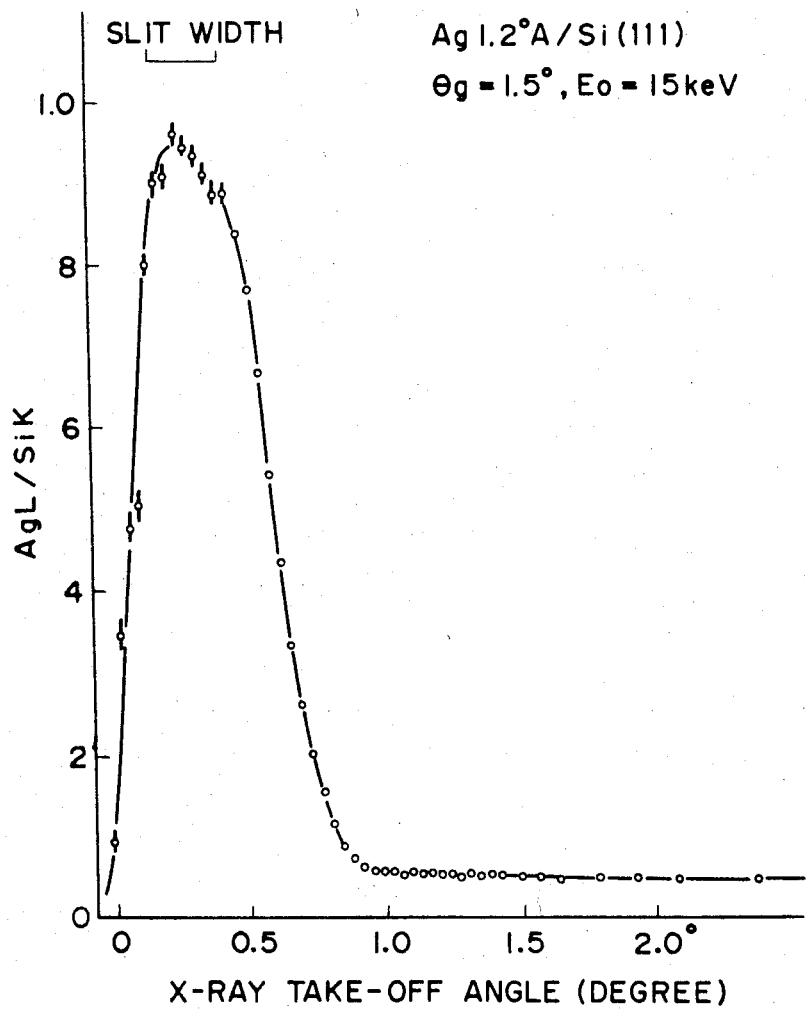
FIG. 5 is an explanatory view of the relationship between the take-off angle of the X-ray and the ratio of the line SiK$\alpha$ and the line AgL$\alpha\beta$.

FIG. 3 shows the sample shown in FIG. 2 with the vicinity of its surface enlarged. FIG. 4 shows an example of measurement of the distribution of the X-ray energy which is radiated from a sample of Si(111) with Ag 1.2 Å thick (one atomic layer) absorbed on the surface thereof, and FIG. 5 is an explanatory view of the relationship between the take-off angle of the X-ray and the ratio of the line SiK$\alpha$ and the line AgL$\alpha\beta$.

The electron beam which enters the surface diffuses while repeating scattering by virtue of interaction with atoms, as shown in FIG. 2, and therefore the X-ray radiated by the excitation of the electron beam is produced from the range such as shown in FIG. 2. Since the ordinary penetrating power of the X-ray is more than 1 μm, in the conventional method of detecting an X-ray at a large take-off angle with an X-ray detector 21 or 22, (FIG. 3) even if the diameter of an electron beam is minimized, the electrons which have entered a crystal assume multiple scattering and diffuse, such that unfortunately all the X-rays radiated from the area such as shown by the hatched lines in FIG. 3 are detected. Accordingly, the resolution of the scanning line of the X-ray obtained, whether by the reflection method using the X-ray detector 21 or by the transmission method using the X-ray detector 22, is not more than that of the X-ray at the area where it is produced. Conventionally the take-off angle is several tens of degrees and at the smallest several degrees. This is based on the recognition that the intensity of an X-ray does not vary greatly depending on the degree of the take-off angle, and a large take-off angle is adopted which does not require precise positioning. Accordingly, in an apparatus for analyzing elements on a surface, the detector is also arranged such that the take-off angle is large.

The inventors of the present invention have found, as described above, that in detecting the X-ray radiated from a surface by the excitation of an electron beam, the X-rays radiated from the atoms on the outermost surface can be detected with greatly improved sensitivity by utilizing the total reflection of the X-ray, and have proposed a method of analyzing elements on a surface utilizing this method of detecting an electromagnetic wave at the total reflection angle thereof using detector 23 at or near the total reflection angle. It will be made clear from the example shown in FIG. 4 in which the energy distribution is measured of the X-rays is measured which are radiated from a sample of Si (111) with Ag 1.2 Å thick (one atomic layer) absorbed on the surface thereof. In FIG. 4, the line AgL$\alpha\beta$ of the surface Ag of the sample forms a peak protruding from the background B. The curve d shows the case in which the take-off angle $\beta$ is comparatively large, and the take-off angle $\beta$ is made smaller and approaches a take-off angle $\theta_0$ equivalent to the total reflection angle or an angle in the vicinity thereof in the order of c, b, and a. It should be noted that the peak of a shows the intensity equivalent to the line SiK$\alpha$ of the bulk. Changes of values of the ratio of line AgL$\alpha\beta$ to the line SiK$\alpha$ observed when the take-off angle $\beta$ is decreased from the vicinity of 1.0° are shown in FIG. 5. As is clear from FIG. 5, "a take-off angle $\theta_0$ equivalent to the total reflection angle or an angle in the vicinity thereof" is recognized at an angle not greater than 1.0°. In this example, Ag 1.2 Å thick (one atomic layer) is absorbed onto the surface of Si(111), but the same is applicable to other samples and elements. Accordingly, analysis of elements on a surface at high sensitivity is enabled by determining the take-off angle on the vicinity of the total reflection angle of an X-ray.

As described above, if an electron beam, the spot size of which is converged to the size of approximately an atom (e.g., 3Å) or smaller, is irradiated onto a surface, as shown in FIG. 3, only the X-rays radiated from one to several atoms on the surface can be detected. Scanning the surface of the sample in the directions x and y by means of the electron beam enables observation of the arrangement of the atoms on the outermost surface. An image of the arrangement of atoms for each kind of atom is observed by taking out the characteristic X-lines as signals in this way and forming the scanned image. If the take-off angle of the X-line is varied, it is possible to observe an image of the arrangement of atoms obtained when the depth of the surface layer where the atoms to be detected exist is selectively varied.

As is clear from the above explanation, according to a method of and apparatus for observing the arrangement of atoms on a surface, if an electron beam is converged to approximately 3 Å (the size of an atom), an individual atom can be observed, and even if the electron beam has a diameter more than 5 Å, the above-described surface ultrastructure which is called "7×7 structure", or various kinds of ultrastructures formed by absorbing a metal such as gold, silver, nickel or indium can be observed. Accordingly, with respect to an individual element, the content of the structure, for example, a position where indium is, or the size of the unit, can be observed. It is possible to observe an image of a characteristic X-ray, corresponding to an electron nucleus such as K, L, M , if the electron beam is made to have a diameter smaller than 3 Å, for example, about 1 Å.

If a plurality of X-ray detectors are disposed around a sample, of if an X-ray detector is arranged such as to surround a sample, it is also possible to measure with higher sensitivity by increasing the efficiency of detection of the X-ray which is radiated from the surface of a sample.

It goes without saying that a method and apparatus for observing the arrangement of atoms on a surface is not restricted to the above-described embodiment, but various modifications are possible. This apparatus can be applied to electron microscopes, various kinds of scanning electron microscopes, reflection high energy electron diffraction (RHEED) apparatus, molecular beam epitaxi apparatus, various kinds of X-ray apparatus and other apparatus capable of observation of the arrangement of atoms on a surface, as an elemental analysis apparatus chiefly for solid and liquid surfaces by providing an X-ray detector for detecting an X-ray at a take-off angle equivalent to the total reflection angle of the X-ray with respect to the surface of a sample or an angle in the vicinity thereof. The apparatus for observing the arrangement of atoms on a surface according to the invention provides an observed image of an individual atom and an image of the arrangement of atoms, not on a surface of about several μm as in the prior art, but on the outermost surface of one to several atomic layers. The apparatus and method according to the present invention have characteristics superior to any conventional one, and can contribute to basic and applicative researches in man fields such as studies on a surface of a compound or an alloy. They are widely applicable to a field of basic study such as physics, chemistry, metallurgy, and electronics, and semiconductor industry, metal industry, catalyst industry, atomic power industry, and other technical fields.

As is clear from the above description, the present invention enables observation of the arrangement of atoms on the outermost surface of a solid, which is difficult for a conventional electron microscope to accomplish, as it is for a field ion emission microscope with susbtances other than high-melting-point metals. According to the present invention, the arrangement of atom classified by kind and by characteristic X-lines can also be observed. It is also possible to observe the arrangement of atoms which are not arranged regularly, unlike in a crystal. In addition, since the arrangement of atoms on different surface layers can be observed by varying the take-off angle, observation of a stereoscopic arrangement of atoms in the vicinity of a surface is possible. Thus, various structures on the outermost surface of a solid can be observed in accordance with the diameter of an electron beam.

As many apparently widely different embodiments of the present invention can be made without departing from the spirit and scope thereof, it is to be understood that the invention is not limited to the specific embodiments thereof except a defined in the appended claims.

What we claim is:

1. A method of observing the arrangement of atoms on the surface of a sample comprising the steps of:
    scanning two-dimensionally the surface of a sample by irradiating a finely converged electron beam thereon;
    detecting the X-ray emitted from said surface of said sample by the irradiation of said electron beam at a take-off angle substantially equivalent to the total reflection angle of said X-ray on said surface of said sample; and
    forming a scanned image from the detected electromagnetic wave.

2. A method of observing the arrangement of atoms on a surface according to claim 1, wherein said take-off angle of said X-ray emitted from said surface of said sample is varied.

3. A method of observing the arrangement of atoms on a surface according to claim 1, wherein the diameter of said electron beam for scanning two-dimensionally said surface of said sample is varied.

* * * * *